US012714737B2

(12) United States Patent
Sathe et al.

(10) Patent No.: US 12,714,737 B2
(45) Date of Patent: Aug. 25, 2026

(54) RECOMBINANT PROTEINS, COMPOSITIONS AND METHODS OF STABILIZATION THEREOF

(71) Applicant: UNICHEM LABORATORIES LTD, Mumbai (IN)

(72) Inventors: Dhananjay Sathe, Thane (IN); Vivek Mishra, Sagar (IN); Saravanakumar Iyappan, Hyderabad (IN); Sunil Jog, Mumbai (IN)

(73) Assignee: Unichem Laboratories Ltd, Mumbai (IN)

( * ) Notice: Subject to any disclaimer, the term of this patent is extended or adjusted under 35 U.S.C. 154(b) by 327 days.

(21) Appl. No.: 18/577,495

(22) PCT Filed: Jul. 7, 2022

(86) PCT No.: PCT/IB2022/056276
§ 371 (c)(1),
(2) Date: Jan. 8, 2024

(87) PCT Pub. No.: WO2023/281432
PCT Pub. Date: Jan. 12, 2023

(65) Prior Publication Data

US 2024/0325491 A1 Oct. 3, 2024

(30) Foreign Application Priority Data

Jul. 8, 2021 (IN) ............................ 202121030619

(51) Int. Cl.
*A61K 47/26* (2006.01)
*A61J 1/06* (2006.01)
*A61K 38/17* (2006.01)
*A61K 47/18* (2017.01)

(52) U.S. Cl.
CPC ........... *A61K 38/1732* (2013.01); *A61J 1/065* (2013.01); *A61K 47/183* (2013.01); *A61K 47/26* (2013.01)

(58) Field of Classification Search
CPC ................................................ A61K 38/1732
See application file for complete search history.

(56) References Cited

U.S. PATENT DOCUMENTS

2011/0100861 A1 5/2011 Manabe et al.
2024/0325491 A1 * 10/2024 Sathe .................... A61K 47/26

FOREIGN PATENT DOCUMENTS

WO WO2021005500 A1 1/2021

* cited by examiner

*Primary Examiner* — Tekchand Saidha
(74) *Attorney, Agent, or Firm* — Choi Capital Law; Kevin J Fournier

(57) ABSTRACT

The present invention relates to recombinant proteins, compositions and methods of stabilization thereof. The invention specifically relates to the stable recombinant protein of SEQ ID NO: 1 and composition comprising recombinant protein of SEQ ID NO: 1. The invention further relates to method of preparing, storing and stabilizing recombinant protein of SEQ ID NO: 1 and its composition for longer shelf life.

4 Claims, 4 Drawing Sheets

Specification includes a Sequence Listing.

SEQUENCE LISTING

```
Sequence total quantity: 7
SEQ ID NO: 1            moltype = AA  length = 141
FEATURE                 Location/Qualifiers
source                  1..141
                        mol_type = protein
                        organism = synthetic construct
SEQUENCE: 1
TYKITVRVYQ TNPDAFFHPV EKTVWKYANG GTWTITDDQH VLTMGGSGTS GTLRFHADNG  60
ESFTATFGVH NYKRWCDIVT NLAADETGMV INQQYYSQKN REEARERQLS NYQVKNAKGR  120
NFQIVYTEAE GNDLHANLII G                                            141

SEQ ID NO: 2            moltype = AA  length = 142
FEATURE                 Location/Qualifiers
source                  1..142
                        mol_type = protein
                        organism = synthetic construct
SEQUENCE: 2
MTYKITVRVY QTNPDAFFHP VEKTVWKYAN GGTWTITDDQ HVLTMGGSGT SGTLRFHADN  60
GESFTATFGV HNYKRWCDIV TNLAADETGM VINQQYYSQK NREEARERQL SNYQVKNAKG  120
RNFQIVYTEA EGNDLHANLI IG                                           142

SEQ ID NO: 3            moltype = AA  length = 143
FEATURE                 Location/Qualifiers
source                  1..143
                        mol_type = protein
                        organism = synthetic construct
SEQUENCE: 3
OMTYKITVRV YQTNPDAFFH PVEKTVWKYA NGGTWTITDD QHVLTMGGSG TSGTLRFHAD  60
NGESFTATFG VHNYKRWCDI VTNLAADETG MVINQQYYSQ KNREEARERQ LSNYQVKNAK  120
GRNFQIVYTE AEGNDLHANL IIG                                          143

SEQ ID NO: 4            moltype = AA  length = 144
FEATURE                 Location/Qualifiers
source                  1..144
                        mol_type = protein
                        organism = synthetic construct
```

-continued

```
SEQUENCE: 4
OOMTYKITVR VYQTNPDAFF HPVEKTVWKY ANGGTWTITD DQHVLTMGGS GTSGTLRFHA  60
DNGESFTATF GVHNYKRWCD IVTNLAADET GMVINQQYYS QKNREEARER QLSNYQVKNA  120
KGRNFQIVYT EAEGNDLHAN LIIG                                         144

SEQ ID NO: 5            moltype = AA  length = 144
FEATURE                 Location/Qualifiers
source                  1..144
                        mol_type = protein
                        organism = synthetic construct
SEQUENCE: 5
OMTYKITVRV YQTNPDAFFH PVEKTVWKYA NGGTWTITDD QHVLTMOGGS GTSGTLRFHA  60
DNGESFTATF GVHNYKRWCD IVTNLAADET GMVINQQYYS QKNREEARER QLSNYQVKNA  120
KGRNFQIVYT EAEGNDLHAN LIIG                                         144

SEQ ID NO: 6            moltype = AA  length = 145
FEATURE                 Location/Qualifiers
source                  1..145
                        mol_type = protein
                        organism = synthetic construct
SEQUENCE: 6
OOMTYKITVR VYQTNPDAFF HPVEKTVWKY ANGGTWTITD DQHVLTMOGG SGTSGTLRFH  60
ADNGESFTAT FGVHNYKRWC DIVTNLAADE TGMVINQQYY SQKNREEARE RQLSNYQVKN  120
AKGRNFQIVY TEAEGNDLHA NLIIG                                        145

SEQ ID NO: 7            moltype = AA  length = 146
FEATURE                 Location/Qualifiers
source                  1..146
                        mol_type = protein
                        organism = synthetic construct
SEQUENCE: 7
OOMTYKITVR VYQTNPDAFF HPVEKTVWKY ANGGTWTITD DQHVLTMOGG SGTSGTLRFH  60
ADNGESFTAT FGVHNYKRWC DIVTNLAADE TGMOVINQQY YSQKNREEAR ERQLSNYQVK  120
NAKGRNFQIV YTEAEGNDLH ANLIIG                                       146
```

RECOMBINANT PROTEINS, COMPOSITIONS AND METHODS OF STABILIZATION THEREOF

FIELD OF INVENTION

The present invention relates to the recombinant lectin protein derived from *Sclerotium rolfsii* lectin, its compositions, and methods for improving their stability.

BACKGROUND OF INVENTION

Lectins are highly specific carbohydrate-binding proteins, macromolecules that are highly specific for sugar moieties of other molecules. Many lectins are used as biomarkers indicating early detection of malignant growth or as autophagy inducers while Other lectins also show the ability to inhibit cancerous growth through apoptosis. Lectins modulate cancer associated pathways, and they have potential as cancer diagnostic and therapeutic agents. Currently, most commercially available lectins are from plants and other eukaryotes.

*Sclerotium rolfsii* lectin (or "SRL") is a lectin that has been isolated from the sclerotial bodies of the soil-borne phytopathogenic fungus *Sclerotium rolfsii*. SRL has specificity towards Thomsen-Friedenreich (TF) antigen and Tn antigen. TF antigen is a disaccharide (Galβ1→3GalNAc-α-Ser/Thr) that is over-expressed on the cell surface of different human cancer cells. Tn antigen is a monosaccharide (GalNAc-α-Ser/Thr). It is known that TF and Tn are involved in the adhesion of tumour cells to the endothelium via a mechanism recruiting Galectin-3 and MUC-1, which is the first step in metastasis formation. Furthermore, it became clear that this pathway can be blocked by a growing number of molecules, thereby creating ways of therapeutical intervention. Due to its specificity for TF and Tn antigen, SRL has been shown to bind to human cancer cells.

WO/2010/095143, WO/2014/203261 and WO/2020/044296 discloses several recombinant variants of SRL, contents whereof are incorporated herein, in entirety, by way of reference. Apart from exhibiting improved specificity towards TF and Tn antigen compared to native SRL, the new variants have demonstrated high solubility and stability. Therapeutic use of these variants for cancer has been disclosed in above listed applications. WO/2020/074984 further discloses therapeutic use of such variants for treatment or prevention of inflammatory diseases, contents whereof is incorporated herein, in its entirety, by way of reference.

Pharmaceutical proteins and polypeptides, among other biopharmaceuticals, pose formulation challenges due to stability issues. Proteins in conventional solutions generally are unstable. They are prone to degradation, such as oxidation deamidation, aggregation and precipitation, from both chemical and physical processes. Aggregation, precipitation, coagulation and viscosity are particularly problematic for most proteins, especially at high protein concentrations. Proteins generally are more stable when lyophilized than they are in solution. However, instability during storage & transportation limit the successful marketing of various protein formulations.

The basic principle of pharmaceutical protein preparations is that certain instability must be overcome. Proteolytic pathways can be divided into two different classes, including chemical and physical instability. Chemical instability results in protein modification through bond formation or cleavage. Examples of chemical instability problems include deamidation, racemization, hydrolysis, oxidation, β-elimination and disulfide exchange. Physical instability, on the other hand, does not result in covalent changes in the protein; rather, physical instability is associated with changes in the higher-order structure (secondary and higher) of the protein. These include denaturation, surface adsorption, aggregation and precipitation. (Manning et al., Pharma. Res. 6,903 (1989)). Moreover, certain proteins are sensitive when exposed to ambient atmospheric conditions and/or to UV light during production, formulation and storage, which can lead to protein degradation and potentially affect the potency of a formulation. For instance, the photoirradiation of proteins can lead to aggregation, oxidation, fragmentation, and reduced bioactivity.

Although WO/2010/095143 and WO/2014/203261 addressed stability issues related to native SRL by modifying the sequence, the modified recombinant lectins did not exhibit the stability that was required for handling and formulating the drug product. The recombinant lectins were further stabilised using stabilizers in the formulation as disclosed in WO/2021/005500, contents whereof is incorporated herein, in its entirety, by way of reference. However, the proteins still presented a challenge with respect to stability during formulation, storage or transportation, which often got aggregated or oxidized in the process.

A pharmaceutical formulation must be stable at room temperature, should be easy to handle and should have a longer shelf life for it to be easy for transport, storage and handling. Aggregate formation, oxidation, coagulation and/or precipitation by a protein during storage and handling of a pharmaceutical composition can adversely affect biological activity of the protein, resulting in loss of therapeutic efficacy of the pharmaceutical composition.

OBJECT OF THE INVENTION

Therefore, it is an object of the present invention to provide recombinant lectin protein that exhibits long-term stability at room temperature and longer-term stability at temperature lower than room temperature. Such recombinant lectin protein has longer shelf life.

Another object of the present invention is to develop a method for improving the long-term stability of the recombinant lectin protein, particularly a recombinant lectin protein derived from SRL.

Yet another object of the present invention is to develop a stable, pharmaceutically acceptable, therapeutically effective formulation of recombinant lectin. Particularly it is an object to provide a lectin formulation which is stable for long-term at room temperature and for longer-term at temperature lower than room temperature.

A further object is to provide a stable lyophilized lectin formulation with improved stability which is easy to handle, storage and delivery during its shelf life.

It is another object of the present invention, to provide a process to prepare a stable, pharmaceutically acceptable, therapeutically effective formulation of recombinant lectin.

Another object of the present invention is to develop a method for improving the long-term stability of the formulation comprising recombinant lectin protein.

SUMMARY OF THE INVENTION

According to a first aspect, the present invention provides a stable lectin protein of SEQ ID NO: 1 comprising less than 5% of high molecular weight impurities or related substance impurities individually or in combination when stored at least for a period of about 6 months at a temperature from about 20° C. to about 25° C. and relative humidity of about 60%; wherein the lectin protein is stored in an airtight container that obstructs/resists light waves having wavelength ranging from about 100 nm to about 500 nm; and wherein the headspace in the container comprises an inert atmosphere or vacuum.

According to a second aspect, the present invention provides a lectin protein of SEQ ID NO: 1 comprising less than 5% of high molecular weight impurities or related substance impurities individually or in combination when stored at least for a period of about 1 year at a temperature from about 2° C. to about 8° C.; wherein the lectin protein is stored in an airtight container that obstructs/resists light waves having wavelength ranging from about 100 nm to about 500 nm; and wherein the headspace in the container comprises vacuum or an inert atmosphere.

According to a third aspect of the invention, there is provided a method of improving the stability of the lectin protein of SEQ ID NO: 1, wherein the method comprises storing the lectin protein of SEQ ID NO: 1 in an airtight container that obstructs/resists light waves having wavelength ranging from about 100 nm to about 500 nm; and wherein the headspace in the container comprises vacuum or an inert atmosphere, further wherein the lectin protein of SEQ ID NO: 1 comprises less than 5% of high molecular weight impurities or related substance impurities individually or in combination after storage in the said container at least for a period of about 6 months at a temperature from about 20° C. to about 25° C. and relative humidity of about 60%.

According to a fourth aspect of the invention, there is provided a method of improving the stability of the lectin protein of SEQ ID NO: 1, wherein the method comprises storing the lectin protein of SEQ ID NO: 1 in an airtight container that obstructs/resists light waves having wavelength ranging from about 100 nm to about 500 nm, the headspace in the container comprising vacuum or an inert atmosphere, and wherein the lectin protein of SEQ ID NO: 1 comprises less than 5% of high molecular weight impurities or related substance impurities individually or in combination after storage in the said container at least for a period of about 1 year at a temperature from about 2° C. to about 8° C.

According to a fifth aspect of the invention, there is provided a composition comprising lectin protein of SEQ ID NO: 1 and a stabilizer, wherein the composition comprises less than 5% of high molecular weight impurities or related substance impurities individually or in combination when stored at least for a period of about 6 months at a temperature from about 20° C. to about 25° C. and relative humidity of 60%; wherein the composition is stored in an airtight container that obstructs/resists light waves having wavelength ranging from about 100 nm to about 500 nm; and wherein the headspace in the container comprises vacuum or an inert atmosphere.

According to a sixth aspect of the invention, there is provided a composition comprising lectin protein of SEQ ID NO: 1 and a stabilizer, wherein the composition comprises less than 5% of high molecular weight impurities or related substance impurities individually or in combination when stored at least for a period of about 1 year at a temperature from about 2° C. to about 8° C., wherein the composition is stored in an airtight container that obstructs/resists light waves having wavelength ranging from about 100 nm to about 500 nm; and wherein the headspace in the container comprises vacuum or an inert atmosphere.

According to a seventh aspect of the invention, there is provided a lyophilized composition comprising:

a) a lectin protein of SEQ ID NO: 1, and
b) a stabilizer, consisting essentially of an amino acid or its salt, a surfactant, a sugar or carbohydrate or combination thereof, wherein, the composition, when placed in an airtight container that obstructs/resists light waves having wavelength ranging from about 100 nm to about 500 nm and the headspace in the container is vacuum or an inert atmosphere, is stable at least for a period of about 6 months at temperature from about 20° C. to about 25° C. and relative humidity of about 60%, and wherein, after such a period, the composition exhibits less than 5% of high molecular weight impurities or related substance impurities individually or in combination.

According to an eighth aspect of the invention, there is provided a lyophilized composition comprising:

a) a lectin protein of SEQ ID NO: 1, and
b) a stabilizer, consisting essentially of an amino acid or its salt, a surfactant, a sugar or carbohydrate or combination thereof, wherein, the composition, when placed in an airtight container that obstructs/resists light waves having wavelength ranging from about 100 nm to about 500 nm and the headspace in the container is vacuum or an inert atmosphere, for a period of about 1 year at a temperature from about 2° C. to about 8° C., the composition exhibits less than 5% of high molecular weight impurities or related substance impurities individually or in combination.

According to one of the aspect of the present invention there is provided a stable pharmaceutical composition comprising:

a) about 0.0001% (w/v) to about 10% (w/v) of a recombinant lectin protein derived from *Sclerotium rolfsii* lectin; and
b) about 0.01% (w/v) to about 10% (w/v) of one or more amino acids or pharmaceutically acceptable salt thereof;
c) about 0.0001% (w/v) to about 1% (w/v) of one or more surfactants; or
d) about 0.1% (w/v) to about 15% (w/v) of one or more carbohydrates or sugars.

The percentage used herein refers to the amount (weight) of the component in the final formulation in volume ready for administration. The percentage may be determined by the methods known in the prior art.

According to a ninth aspect of the invention, there is provided a stable, lyophilized parenteral composition comprising:

a) about 0.01% w/v to about 2% w/v of a lectin protein of SEQ ID NO: 1,
b) about 0.04% w/v to about 0.8% w/v of polysorbate 80,
c) about 0.08% w/v to about 1.6% w/v of L-arginine hydrochloric acid,
d) about 0.09% w/v to about 19.2% w/v of sucrose, and
e) about 0.09% w/v to about 20% w/v of mannitol, wherein, the composition when placed in an airtight container that obstructs/resists light waves having wavelength ranging from about 100 nm to about 500 nm and the headspace in the container comprises vacuum or an inert atmosphere, is stable at least for a period of about 6 months at a temperature from about 20° C. to about 25° C. and relative humidity of about 60%, wherein, after such period, the composition exhibits less than 5% of high molecular weight impurities or related substance impurities individually or in combination.

According to a tenth aspect of the invention, there is provided a stable, lyophilized parenteral composition comprising:

a) about 0.01% w/v to about 2% w/v of a lectin protein of SEQ ID NO: 1,
b) about 0.04% w/v to about 0.8% w/v of polysorbate 80,
c) about 0.08% w/v to about 1.6% w/v of L-arginine hydrochloric acid,
d) about 0.09% w/v to about 19.2% w/v of sucrose, and
e) about 0.09% w/v to about 20% w/v of mannitol, wherein, the composition, when placed in an airtight container that obstructs/resists light waves having wavelength ranging from about 100 nm to about 500 nm and the headspace in the container is vacuum or an inert atmosphere, is stable at least for a period of about 1 year at a temperature from about 2° C. to about 8° C., wherein, after such period, the composition exhibits less than 5% of high molecular weight impurities or related substance impurities individually or in combination.

According to an eleventh aspect of the present invention, there is provided an airtight container that obstructs/resists light waves having wavelength ranging from about 100 nm to about 500 nm, comprising a lectin protein of SEQ ID NO: 1 or composition thereof and a headspace, wherein the headspace is vacuum or an inert atmosphere.

According to twelfth aspect of the present invention, there is provided a method of packaging a lectin protein of SEQ ID NO 1 or pharmaceutical composition thereof, wherein the method comprises:

a) placing the lectin protein of SEQ ID NO 1 or the composition in a container that obstructs/resists light waves of wavelength between 100 nm to 500 nm, and
b) sealing the container such that the lectin protein of SEQ ID NO 1 or the composition remains in contact with vacuum or an inert atmosphere.

According to a thirteenth aspect of the invention, there is provided a method of preparation of a stable lyophilized composition comprising:

a) lectin protein of SEQ ID NO: 1, and
b) a stabilizer, consisting essentially of an amino acid or its salt, a surfactant, a sugar or carbohydrate or combination thereof, wherein, the method comprises formulating the composition under the light having wavelength of more than about 500 nm.

According to a fourteenth aspect of the invention, there is provided a recombinant lectin protein of SEQ ID NO: 1 substantially free of impurity proteins of Formula I.

According to a fifteenth aspect of the invention, there is provided a composition comprising recombinant lectin protein of SEQ ID NO: 1, wherein the composition is substantially free of impurity proteins of Formula I.

Definitions

Figure 1:
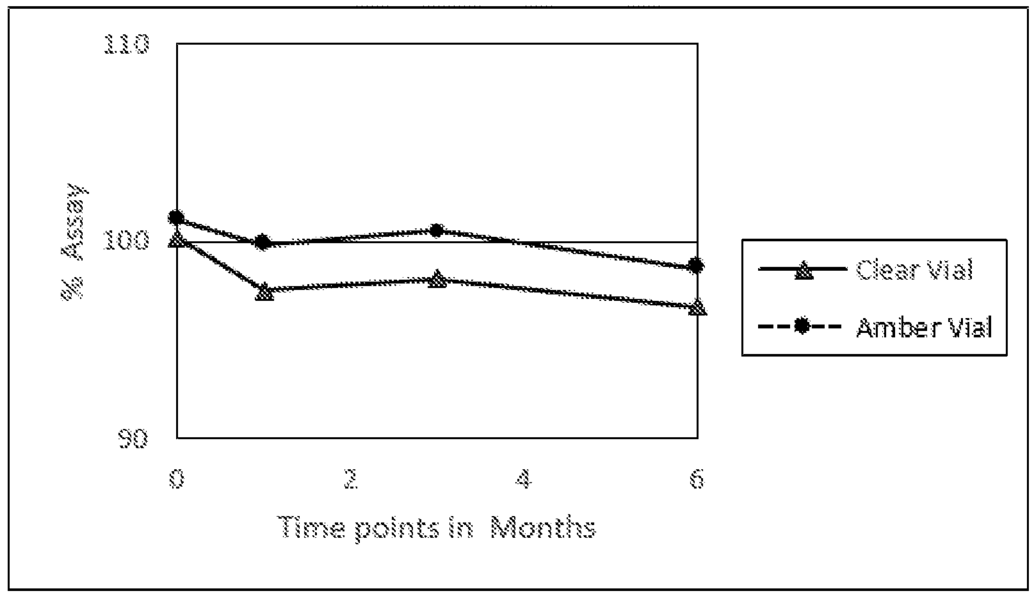
FIG. 1: Assay results of composition stored in Clear versus Amber vial at 25° C./60% RH

As used herein the term "room temperature" refers to a temperature in the range of from 20° C. to 30° C., preferably to a temperature in the range of from 22° C. to 27° C., more preferably to a temperature in the range of from 23° C. to 26° C.

Shelf life is the period of time, from the date of manufacture, that a drug product is expected to remain within its approved product specification while stored under the recommended storage conditions. Shelf life is typically expressed in units of months, i.e. 24 months, 36 months, to a maximum of 60 months. For the purpose of present invention, the shelf life of the lectin protein of SEQ ID NO: 1 is at least 1 month, at least 3 months, at least 6 months, at least 12 months or at least 24 months.

The term "lectin" as used herein refers to a carbohydrate-binding protein, wherein the term "protein" as used herein refers to a polymer of amino acid residues.

The terms 'formulation', 'composition', 'pharmaceutical formulation' and 'pharmaceutical composition' are used interchangeably and refer to preparations which are in such a form as to permit the biological activity of the active ingredients to be effective, and, therefore may be administered to a subject for therapeutic use, wherein the subject is preferably human. 'Active ingredients' as used herein refers to the recombinant lectin or recombinant protein having desired biological or therapeutic activity to free the subject from the disease or symptoms of disease or slow or delay the progression of the disease. The formulation of the present invention are prepared as liquid formulation or solid formulation. A Liquid formulation is in the form of solutions, emulsions or suspensions suitable for oral administration or injection. It will be appreciated by the person skilled in the art that the liquid formulation is in the medium such as water for Injection (WFI) as a liquid vehicle. The solid formulation is either prepared by mixing solid ingredients or by evaporating the solvent medium. The solid formulations can also be prepared by lyophilisation of the liquid formulation, wherein in the process of lyophilisation, material to be dried is first frozen and then the ice or frozen solvent is removed by sublimation under vacuum or an inert atmosphere. For stability reasons, excipients may be added in the formulation before it is lyophilised. During lyophilisation it may be necessary to identify and employ appropriate shelf temperatures, product temperatures, vacuum levels, freezing, primary drying parameters, and secondary drying parameters, which is in the ambit of the knowledge of the person skilled in the art. The solid formulation may also be known as lyophilized formulation.

The term "drug product" refers to a finished dosage form that contains a drug substance, generally, but not necessarily, in association with one or more other excipients. In the context of the present invention, composition comprising a lectin protein of SEQ ID NO: 1 with the excipient is a drug product.

The term "Drug substance" refers to an active ingredient that is intended to furnish pharmacological activity or other direct effect in the diagnosis, cure, mitigation, treatment, or prevention of disease or to affect the structure or any function of the human body, but does not include intermediates used in the synthesis of such ingredient. For the purpose of the present invention, drug substance is a lectin protein of SEQ ID NO: 1.

The term "Container" relates to the object that holds the contents of the drug or composition. Container such as vial, syringe, cartridge or ampule, wherein such container resists/obstructs light waves of wavelength 100-500 nm or is opaque. In the context of the present invention, the container is an airtight container and is dark coloured such as black, blue, red or amber coloured and obstructs/resists light waves having wavelengths ranging from about 100 nm to about 500 nm. For the purpose of the present invention, the container is a light resistant amber coloured container comprising a lectin protein of SEQ ID NO: 1 or composition thereof with stabilizing agents that obstructs/resists both ultra-violate (uv) and near visible light waves having wavelengths ranging from about 100 nm to about 500 nm. It is envisaged that the container may be made of glass material, particularly of type I, II, III or IV glass.

The term "Light resistant" relates to a container-closure system that protects the contents from the effects of light by virtue of the specific properties of the material of which it is composed, including any coating applied to it. In the context of the present invention, light resistant container is an amber colour vial that obstructs/resists both ultra-violate (uv) and near visible light waves having wavelength from about 100 nm to about 500 nm.

The term "opaque" relates to the ability or property of the material to block the passage of light. For the purpose of the present invention the term opaque refers to the material that is semi-opaque or partially opaque. Such material is impervious or partially impervious to light.

The term inert atmosphere means 'chemically inactive' atmosphere. The inert atmosphere may comprise of vacuum or non-reactive gas atmosphere, such as nitrogen, carbon dioxide, argon, helium, etc.; used to blanket the composition in storage, to purge process lines and vessels of reactive gases and liquids, and to cover a mix in a partially filled vessel. In the context of the present invention, container comprising a lectin protein of SEQ ID NO: 1 or composition thereof has headspace that comprises vacuum or an inert atmosphere.

The term "Assay" relates to quantitative estimation of drug substance present in the drug product by suitable analytical method known in the art. In the context of the present invention 'assay' is the analysis for determination of quantitative estimation of the lectin protein of SEQ ID NO: 1 in a composition by High Performance Liquid chromatography (HPLC) method.

The term "diluent" is a diluting agent used to dilute a medication. A diluent may be a liquid for the dissolution of drugs to be injected, ingested, or inhaled. Diluent may be normal saline (NS), sterile water for injection (SWFI), Dextrose 5% in water (D5W). In the context of the present invention lyophilized formulation may be reconstituted with suitable pharmaceutically acceptable diluent or mixture thereof to get required concentration as known by the skilled person. More preferably, diluent is a sterile water for injection.

The term "stabilizer" or "stabilizing agents" relates to the excipients of the composition of the present invention. In the context of the present invention are understood as disclosed in WO2021/005500.

DESCRIPTION OF THE INVENTION

Sequence Listing

```
SEQ ID NO: 1:
represents a variant of the
S. rolfsii lectin amino acid sequence
TYKIT VRVYQ TNPDA FFHPV EKTVW

KYANG GTWTI TDDQH VLTMG GSGTS

GTLRF HADNG ESFTA TFGVH NYKRW

CDIVT NLAAD ETGMV INQQY YSQKN

REEAR ERQLS NYQVK NAKGR NFQIV

YTEAE GNDLH ANLII G

SEQ ID NO: 2:
represents a variant (Met-Lectin) of
SEQ ID NO: 1 with amino acid sequence:
MTYKI TVRVY QTNPD AFFHP VEKTV

WKYAN GGTWT ITDDQ HVLTM GGSGT

SGTLR FHADN GESFT ATFGV HNYKR

WCDIV TNLAA DETGM VINQQ YYSQK

NREEA RERQL SNYQV KNAKG RNFQI

VYTEA EGNDL HANLI IG
```

According to an aspect, the present invention provides a stable lectin protein.

Lectin protein of SEQ ID NO: 1 was first disclosed in Indian patent application 350/MUM/2009 as Rec 2, which was derived from *Sclerotium rolfsii* lectin (SRL).

In an embodiment, the present invention provides a stable, recombinant lectin protein of SEQ ID NO: 1.

The term "recombinant" means a nucleic acid or a polypeptide has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well-known molecular biological procedures. A "recombinant DNA molecule" is comprised of segments of DNA joined together by means of such molecular biological techniques. The term "recombinant protein" or "recombinant polypeptide" as used herein refers to a protein molecule which is expressed using a recombinant DNA molecule. The protein of present invention can be expressed in bacteria or yeast.

In an embodiment the recombinant lectin protein of SEQ ID NO: 1 is intended here to cover lectin proteins with more than 85% homology to SEQ ID NO: 1. The term "homology" as used herein refers to the lectin protein that shares at least 85% of identity with SEQ ID NO: 1 over a given region or portion of sequence. The percentage homology between SEQ ID NO: 1 and other sequence is determined using the BLASTP algorithm with default parameters (Altschul et al. Nucleic Acids Res. 1997 Sep. 1;25 (17): 3389-402). In particular, the BLAST algorithm can be accessed on the internet using the URL: https://blast.ncbi.nlm.nih.gov/Blast.cgi. In an alternative embodiment, for global sequence alignments, percentage homology between two sequences is determined using the EMBOSS Needle algorithm using default parameters. In particular, the EMBOSS Needle algorithm can be accessed on the internet using the URL: https://www.ebi.ac.uk/Tools/psa/emboss_needle/.

Unless otherwise indicated, the term "homology" is used interchangeably with the term "identity" in the present specification.

In an embodiment, the lectin protein of SEQ ID NO: 1 may include its pharmaceutically acceptable salt, solvate, hydrate, prodrug, or any other pharmaceutically acceptable form. The pharmaceutically acceptable salt, solvate, hydrate, prodrug, or any other pharmaceutically acceptable form of SEQ ID NO: 1 refer to substances which have biological effectiveness same as that of SEQ ID NO: 1 and which do not possess any undesirable properties. The preparation of salts, solvates, hydrates, and prodrugs can be carried out by methods known in the art.

SEQ ID NO:1 can be prepared by the processes disclosed in 350/MUM/2009 or WO/2020/074977. For the purpose of present invention, the lectin protein was prepared and purified by the process disclosed in WO/2020/074977, contents whereof are incorporated herein, in its entirety, by way of reference . . .

According to another aspect, the present invention provides a composition comprising a lectin protein of SEQ ID NO: 1.

In another embodiment, the present invention provides a composition comprising recombinant lectin protein of SEQ ID NO:1.

In an embodiment, the invention provides a composition comprising recombinant lectin protein SEQ ID NO: 1 and a stabilizer.

According to an aspect of the invention the stabilizer may be selected from surfactants, detergents, amino acids, pharmaceutically acceptable salt of amino acid, carbohydrates or sugar stabilizers, amines, polyols or combination thereof.

According to this embodiment the non-limiting examples of surfactants are Tween® 20 (Polysorbate 20), Tween® 40 (Polysorbate 40), Tween® 60 (Polysorbate 60), Tween® 80 (Polysorbate 80), Sorbitan monolaurate, Sorbitanmonopalmitate, Sorbitan monostearate, Sorbitantristearate, Sorbitan monooleate, Triton™ X-100, Pluronic® F-68, Pluronic® F-88, Pluronic® F-127 (poloxamers), Sorbitan Monolaurate, SorbitanMonosterate, Sorbitantristearate, Poloxamer 188 and Brij 35 (polyoxyethylene alkyl ether) or combination thereof.

In some embodiment, the surfactant may be in the range from 0.001 mg/ml to 10 mg/ml or from 0.0001% (w/v) to 1.0% (w/v).

In some embodiment, a stable composition comprises recombinant lectin derived from *Sclerotium rolfsii* lectin and one or more surfactant, wherein the ratio of protein to surfactant is in the range from 1:0.0002 to 1:10.

Further, according to an embodiment, the amino acid may be selected from glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, arginine or combination thereof. The amino acid may be L-amino acid or D-amino acid, preferably L-amino acid. The amino acid may be used as such or as its salt. The salt may be an alkali salt or an alkaline earth metal salts, ammonium salts, organic amine salts such as triethylamine salt or triethanolamine salt, arginine salt such as basic amino acid salts or acid salts for example, hydrochloride, hydrobromide, sulfate, nitrate, phosphate, mineral acid salts citric acid salt, oxalate, tartrate or any other salt of amino acid as known to the skilled person. In one embodiment, the amino acid is selected from L-Histidine, L-Arginine, Glutamic acid or Methionine. In another embodiment, the amino acid is a hydrochloride salt of amino acid selected from L-Histidine, L-Arginine, Glutamic acid or Methionine. In a preferred embodiment the amino acid is selected from hydrochloride salt of L-Histidine or L-Arginine.

In some embodiments the concentration of amino acid or its pharmaceutically acceptable salt is in the range of 0.01% (w/v) to 10% (w/v) or from 0.1 mg/ml to 100 mg/ml.

In another embodiment, a stable composition comprises recombinant lectin derived from *Sclerotium rolfsii* lectin and one or more amino acid or its pharmaceutically acceptable salt. The ratio of protein to amino acid or its pharmaceutically acceptable salt is in the range from 1:0.1 to 1:10.

According to yet another embodiment, the carbohydrate or sugar stabilizers may be selected from the non-limiting examples of sucrose, trehalose, sorbitol, glycerol, mannitol, lactose, xylitol, arabitol, erythritol, lactitol, maltitol, Glucose, Raffinose, Maltose, dextran, inositol or combinations thereof. In some embodiments, the carbohydrate is sucrose or mannitol. In another embodiment the concentration of carbohydrate is in the range from 0.1% (w/v) to 15% (w/v) or from 1.0 mg/ml to 150.0 mg/ml.

In yet another embodiment, a stable composition comprises recombinant lectin derived from *Sclerotium rolfsii* lectin and one or more carbohydrate or sugar stabilizers, wherein the ratio of protein to carbohydrate is in the range from 1:0.1 to 1:150.

According to the aspect of the invention the stabilizer may further be selected from Amines like basic proteins such as protamine or pharmaceutically acceptable salt of protamine or natural or synthetic polymers bearing amine-residues such as polylysine. Protamine may be obtained or derived from, for example, human or fish. The stabilizer may also be selected from polyols such as PEG 400 to PEG 20,000, glycerol or xylitol.

In a particularly preferred embodiment, the stabilizer is a combination of one or more of surfactants, amino acids, pharmaceutically acceptable salt of amino acid and/or carbohydrates.

For example, the stabilizer may be a combination of surfactant and amino acid or may be the combination of amino acid or its salt and carbohydrate.

In particular embodiment the present invention provides a composition comprising:

a) a lectin protein of SEQ ID NO: 1, and
b) a stabilizer, consisting essentially of an amino acid or its salt, a surfactant, a sugar or carbohydrate or combination thereof.

In more particular embodiment the present invention provides a composition comprising:

a) about 0.01% w/v to about 2% w/v of a lectin protein of SEQ ID NO: 1,
b) about 0.04% w/v to about 0.8% w/v of polysorbate 80,
c) about 0.08% w/v to about 1.6% w/v of L-arginine hydrochloric acid,
d) about 0.09% w/v to about 19.2% w/v of sucrose, and
e) about 0.09% w/v to about 20% w/v of mannitol, In an embodiment, the lectin protein of SEQ ID NO: 1 or the composition comprising lectin protein of SEQ ID NO: 1 may be stored in a glass container such as vial, syringe, ampule, wherein such container resists light of wavelength between 100 nm-500 nm, or container is opaque. It is well known that glass containers are categorized into Types I, II, III, and IV. Type I Glass Containers contain 10% of boric oxide, 80% of silica, and small quantities of both aluminium oxide and sodium oxide. The boric oxide in it makes it highly hydrolytically resistant and chemically inert. More particularly, Type I glass container is highly suitable for packaging materials for parenteral and non-parenteral preparations. Type II containers have high hydrolytic resistance. Type II glass containers are Type III containers whose inner surface have been treated with sulphur. This treatment helps to prevent weathering from the containers. Type II glass generally has a lower melting point than Type I glass so it is much easier to mould. Type II glass containers are suitable for storing neutral aqueous preparations and acidic preparations whether they are parenteral or non-parenteral. Type III Glass Containers are made of 10% calcium oxide, 15% sodium oxide, and 75% silica. They also contain negligible amounts of aluminium oxide, potassium oxide, and magnesium oxide. While magnesium oxide reduces the temperature required to mould the glass, aluminium oxide improves its chemical durability and are used for packaging non-parenteral preparations and for packaging certain parenteral products. Type IV Glass Containers contains general-purpose soda lime and they have low hydrolytic resistance. This category of glass containers is the best for products that are meant to be autoclaved because the rate of erosion reaction of the glass containers will be increased. Type IV glass containers are used for the storage of oral dosage forms and topical products. In particular, in the present invention the container is Type I container.

In an embodiment, the lectin protein of SEQ ID NO: 1 or the composition comprising lectin protein of SEQ ID NO: 1 may be stored in a container such as vial, syringe, cartridge or ampule, wherein such container resists light of wavelength between 100 nm and 500 nm, or container is opaque. In particular, the container is a dark coloured container such as black, blue, red or amber coloured that obstructs light waves having wavelength ranging from about 100 nm to about 500 nm. Light causes deterioration of many pharmaceutical products due to its transmission from the primary containers. The effect of light increases and is much more harmful as the wavelength of light decreases. Light sensitive products must be packaged in light resistant amber glass and plastic bottles because these are manufactured to absorb light in the UV region to protect the pharmaceutical products. The measurement of light transmission characteristics of glass and plastic bottles is an important consideration in the evaluation of packaging material to protect pharmaceutical products from deterioration. The light transmission can be influenced by altering the chemical composition of glass bottle, so not all amber bottles provide sufficient protection against UV light. The extent to which UV light can cause a photochemical reaction is dependent on its penetration to the system. Radiation energy from artificial sources either UV or visible light significantly affects the stability of photosensitive products, since it accelerates photochemical degradation reactions that have a product deterioration effect. UV rays carry more energy than visible light and cause greater damage. For this reason, organic compounds are used as light stabilizers in a wide variety of plastic resins to prevent photodegradation caused by sunlight and artificial UV light. The amount of residual oxygen in the headspace of the package is sufficient to catalyze photo oxidation reactions that affect certain components of the pharmaceutical products. In the present invention, the headspace of the vial comprises inert atmosphere, wherein the inert atmosphere is selected from vacuum or inert gas(es) like Argon, Nitrogen, etc.

In an embodiment, the lectin protein of SEQ ID NO: 1 or the composition comprising lectin protein of SEQ ID NO: 1 is stable when stored in a container that obstructs/resists light. In particular, the lectin protein of SEQ ID NO: 1 is stable when stored in a container that obstructs/resists both ultra-violate (uv) and near visible light. According to more specific embodiment, the lectin protein of the present invention is stable when stored in a container that obstructs/resists light waves having wavelength ranging from about 100 nm to about 500 nm.

In an embodiment, the lectin protein of SEQ ID NO: 1 or the composition comprising lectin protein of SEQ ID NO: 1 may be stored in a light resistant container such as vial, syringe, cartridge or ampule, or wherein such container is opaque. In particular the container is a dark coloured container such as black, blue, red or amber coloured, that obstructs/resists light waves having wavelength ranging from about 100 nm to about 500 nm. The container may be a glass container, or a container made of materials such as plastic materials for example, cyclic olefin copolymer (COC) or cyclic olefin polymers (COP) or multi-layered plastic containers (polyamide sandwiched between two COP layers).

According to another embodiment the lectin protein of SEQ ID NO: 1 or the composition comprising lectin protein of SEQ ID NO: 1 may be stored in a container such as vial, syringe, cartridge or ampule, wherein such container is not opaque. The container may be stored away from light, preferably in a secondary container made of paper, cardboard, wood, plastic or light obstructing/resisting glass. More preferably, a secondary container may be a carton, a plastic box or an aluminium pouch.

In an embodiment, the container comprising lectin protein of SEQ ID NO: 1 or its composition is an airtight container. The airtight container is a container with an airtight seal, which does not allow air or gas to pass in and out of the container. Such seal, for example may be a rubber stopper. Thus, the conditions in the container are maintained from the time of sealing, throughout storage, handling and until it is opened for use. The container before sealing may be filled with lectin protein of SEQ ID NO: 1 or composition thereof in the form of solution in buffer or in the form of lyophilized solid.

In another embodiment, the headspace of the container comprises vacuum or an inert atmosphere. Headspace is the space in the container between lectin protein of SEQ ID NO: 1 or the composition comprising lectin protein of SEQ ID NO: 1 and the seal. The container may be subjected to vacuum of about 0.05 mbar to 0.2 mbar. Lectin protein of SEQ ID NO: 1 or its composition may be filed in the container in solid form or in the solution form dissolved in buffer. In lyophilisation process, the composition may be subjected to vacuum or an inert atmosphere for a sufficient period of time at suitable temperature to convert headspace into vacuum or an inert atmosphere. However, protein in solution may be subjected to lyophilization process involving freezing, sublimation and drying, wherein the solution is freezed to below-20° C. for about 20 h to 40 h followed by sublimation under vacuum of about 0.05 mbar to 0.2 mbar for up to 60 h and finally dried under vacuum of about 0.05 mbar to 0.2 mbar for up to 20 h.

According to an embodiment of the present invention, the sealed container comprising lectin protein of SEQ ID NO: 1 may be maintained or stored at room temperature. In particular, the sealed container is maintained or stored at a temperature from about 20° C. to about 25° C. and at relative humidity of about 60%.

According to an embodiment, the sealed container comprising composition of present invention comprising lectin protein of SEQ ID NO: 1 may be maintained or stored at room temperature. In particular the sealed container is maintained or stored at a temperature from about 20° C. to about 25° C. and at relative humidity of about 60%.

According to another embodiment, the sealed container comprising lectin protein of SEQ ID NO: 1 may be maintained or stored below room temperature. In a particular embodiment the temperature may be between about 0° C. and about 15° C. In a more particular embodiment, the sealed container comprising lectin protein of SEQ ID NO: 1 is maintained or stored at a temperature form about 2° C. to about 8° C.

According to another embodiment, the sealed container comprising composition of present invention comprising lectin protein of SEQ ID NO: 1 may be maintained or stored below room temperature. In a particular embodiment the temperature may be between about 0° C. and about 15° C. In a more particular embodiment, the sealed container comprising the said composition is maintained or stored at a temperature from about 2° C. to about 8° C.

In a particular embodiment, the lectin protein of SEQ ID NO: 1 is stable when stored in the sealed container of the present invention, at or below room temperature and/or at a relative humidity of about 60%, wherein the lectin protein is stable for at least a period of about 1 month. The lectin protein under said conditions in said sealed container may remain stable for at least about 3 months, about 6 months, about 9 months or about 12 months. In particular the lectin protein is stable for at least a period of about 6 months or 12 months.

In a more particular embodiment, the lectin protein of SEQ ID NO: 1 is stable when stored in the sealed container of the present invention, at room temperature and/or at a relative humidity of about 60%, wherein the lectin protein is stable at least for a period of about 6 months.

In a particular embodiment, the composition comprising lectin protein of SEQ ID NO: 1 is stable when stored in the sealed container of the present invention, at or below room temperature and/or at a relative humidity of about 60%, wherein the composition is stable for at least a period of about 1 month. The composition under said conditions in said sealed container may remain stable for at least about 3 months, about 6 months, about 9 months or about 12 months. In particular the composition is stable for at least a period of about 6 months or 12 months.

In a more particular embodiment, the composition comprising lectin protein of SEQ ID NO: 1 is stable when stored in the sealed container of the present invention as disclosed herein, at room temperature and/or at a relative humidity of about 60%, wherein the lectin protein is stable for at least a period of about 6 months.

In another more particular embodiment, the lectin protein of SEQ ID NO: 1 is stable when stored in the sealed container of the present invention, at 2° C. to 8° C., wherein the lectin protein is stable for at least a period of about 12 months.

In another more particular embodiment, the composition comprising lectin protein of SEQ ID NO: 1 is stable when stored in the sealed container of the present invention, at 2° C. to 8° C., wherein the said composition is stable for at least a period of about 12 months.

In an aspect, the lectin protein of SEQ ID NO: 1 or the composition comprising lectin protein of SEQ ID NO: 1 is said to be stable when stored in the sealed container of the present invention, at or below room temperature and/or at a relative humidity of 60%, at least for the period of not less than 1 month, if it comprise less than 10%, less than 7%, or less than 5% of high molecular weight protein impurities or related substance impurities individually or in combination, after such a period of storage.

In an embodiment, the undesirable forms of SEQ ID NO: 1 may result from self-association, disordered form of proteins, wherein the protein undergoes association with itself to form dimers or higher order oligomers or aggregates. These are known as High Molecular Weight Proteins (HMWP). Such impurities are detected using techniques such as Liquid Chromatography-Mass Spectrophotometer (LCMS), Size exclusion chromatography with UV or Multi-Angle Light Scattering detector (SEC-UV/MALS), Composition-Gradient Multi-Angle static Light Scattering (CG-MALS or CG-SLS), Dynamic light scattering (DLS), Sedimentation equivalent analytical ultra-centrifugation (SE-AUC), Sedimentation velocity analytical ultra-centrifugation (SV-AUC), Gel electrophoresis, Asymmetrical flow field-flow fractionation (AF4), Microflow Imaging or other such method known to the skilled person.

In an embodiment, the lectin protein of SEQ ID NO: 1 or composition comprising lectin protein of SEQ ID NO: 1 is said to be stable when stored in the sealed container of the present invention, at or below room temperature and/or at a relative humidity of about 60%, at least for the period of not less than 1 month, if it comprise less than 10%, less than 7%, less than 5%, or less than 3% of high molecular weight protein impurities after such a period of storage. Particularly the high molecular weight protein impurities are less than 3%.

Other undesirable forms of SEQ ID NO:1 are formed by aggregation, denaturation, degradation or coagulation of the protein. Most of these phenomena occur due to misfolded protein, which is also undesirable. Such forms of protein are known as related substance impurities. Such impurities might differ every time a fresh batch of protein is prepared, handled or stored in unfavourable conditions.

The lectin protein of SEQ ID NO: 1 was prepared and purified by the process disclosed in WO/2020/074977, particularly using the conditions of Batch 5 as given in Table 1 on page 34 of WO/2020/074977. A Met-Lectin, variant of SEQ ID NO: 1, disclosed in WO/2020/074977 is present in the lectin protein of SEQ ID NO: 1 in about 2% to 20%. The amino acid sequence of Met-Lectin is provided at SEQ ID NO: 2. The presence of Met-Lectin of SEQ ID NO: 2 in SEQ ID NO: 1 is particularly disadvantageous because the initiator methionine is highly prone to oxidation. The Sulphur present in methionine undergoes oxidation to form related substance impurities such as impurity proteins of Formula Ia-Ie (SEQ ID NO: 3-7).

A person skilled in the art would appreciate that-according to ICHQ6B guidelines, an inherent degree of structural heterogeneity do occur in proteins due to the biosynthetic processes used by living organisms to produce them; therefore, the desired product can be a mixture of anticipated post-translationally modified forms (e.g., glycoforms). These forms may be active and their presence may have no deleterious effect on the safety and efficacy of the product. Heterogeneity may also arise during manufacture and/or storage of the drug substance or drug product. Since the heterogeneity of these products defines their quality, the degree and profile of this heterogeneity should be characterized, to assure lot-to-lot consistency. When these variants of the desired product have properties comparable to those of the desired product with respect to activity, efficacy and safety, they are considered product-related substances. Due to the unique biosynthetic production process and molecular characteristics of biotechnological and biological products, the drug substance can include several molecular entities or variants. When these molecular entities are derived from anticipated post-translational modification, they are considered as part of the desired product. When variants of the desired product are formed during the manufacturing process and/or storage and have properties comparable to the desired product, they are considered product-related substances and not impurities. A Met-Lectin variant having amino acid sequence as set forth in SEQ ID NO: 2 has been found to remain present in the lectin protein of SEQ ID NO: 1 in an amount of about 2% to about 20% by weight of the lectin protein of SEQ ID NO: 1. Accordingly, the reference herein, throughout the present disclosure, to a lectin protein of SEQ ID NO: 1, a composition comprising a lectin protein of SEQ ID NO: 1 and finished products/packages comprising a lectin protein of SEQ ID NO: 1 are to be construed to be comprising the Met-Lectin variant having amino acid sequence as set forth in SEQ ID NO: 2 in an amount of about 2% to about 20% by weight of the lectin protein of SEQ ID NO: 1.

When lectin protein of SEQ ID NO: 1 was subjected to oxidation using 3% hydrogen peroxide at room temperature for only about 10 min, the protein degraded by more than 14% as compared to the control, hinting towards partial oxidation of methionine at position 44 and 89 in SEQ ID NO: 1. Similarly when lectin protein of SEQ ID NO: 1 with about 12% of Met-lectin variant was exposed to white light of 1.2 million lux hours and near ultraviolet energy of 200-watt hours/square meter for 120 hrs, the protein degraded by 11.74%. On the other hand, it was observed that the composition comprising lectin protein of SEQ ID NO: 1, when exposed to light providing an overall illumination of not less than 1.2 million lux hours and an integrated near ultraviolet energy of not less than 200 wat hours/square meter for the period of 120 hrs, showed formation of around 7-8% of related substance impurities.

In an embodiment the lectin protein of SEQ ID NO: 1, under unregulated conditions, may undergo oxidation to form impurity proteins of Formula I, wherein the impurity proteins of Formula I is a combination of one or more of Formula Ia, Formula Ib, Formula Ic, Formula Id, and/or Formula Ie. Such impurities are formed due to the presence of Met-Lectin protein variant of SEQ ID NO:2.

```
Formula Ia:
(O)MTYKI TVRVY QTNPD AFFHP VEKTV

WKYAN GGTWT ITDDQ HVLTM GGSGT

SGTLR FHADN GESFT ATFGV HNYKR

WCDIV TNLAA DETGM VINQQ YYSQK

NREEA RERQL SNYQV KNAKG RNFQI

VYTEA EGNDL HANLI IG

Formula Ib
(O)(O)MTYKI TVRVY QTNPD AFFHP

VEKTV WKYAN GGTWT ITDDQ HVLTM

GGSGT SGTLR FHADN GESFT ATFGV

HNYKR WCDIV TNLAA DETGM VINQQ

YYSQK NREEA RERQL SNYQV KNAKG

RNFQI VYTEA EGNDL HANLI IG
```

-continued

```
Formula Ic
(O)MTYKI TVRVY QTNPD AFFHP VEKTV

WKYAN GGTWT ITDDQ HVLTM(O)

GGSGT SGTLR FHADN GESFT ATFGV

HNYKR WCDIV TNLAA DETGM VINQQ

YYSQK NREEA RERQL SNYQV KNAKG

RNFQI VYTEA EGNDL HANLI IG

Formula Id
(O)(O)MTYKI TVRVY QTNPD AFFHP

VEKTV WKYAN GGTWT ITDDQ HVLTM(O)

GGSGT SGTLR FHADN GESFT ATFGV

HNYKR WCDIV TNLAA DETGM VINQQ

YYSQK NREEA RERQL SNYQV KNAKG

RNFQI VYTEA EGNDL HANLI IG

Formula Ie
(O)(O)MTYKI TVRVY QTNPD AFFHP

VEKTV WKYAN GGTWT ITDDQ HVLTM(O)

GGSGT SGTLR FHADN GESFT ATFGV

HNYKR WCDIV TNLAA DETGM(O) VINQQ

YYSQK NREEA RERQL SNYQV KNAKG

RNFQI VYTEA EGNDL HANLI IG
```

There is also a significant effect of highly acidic or basic pH on lectin protein of SEQ ID NO: 1. Such extreme environment may disrupt the salt bridges and hydrogen bonding formed between the side chains, leading to denaturation. Highly basic pH may convert the protonated $—NH_3^+$ ion to a neutral $—NH_2$ group, and immediately initiate hydrolysis and degradation by cleaving the amino acids as well as side chains of the molecules. Such forms even at a concentration as less as 10% affect properties and efficacy of the product, making it pharmaceutically undesirable. Some of such forms may have negative effect on the subject, causing harm and long-term irreversible damages. It is therefore desirable that the pharmacopeial grade lectin protein of SEQ ID NO: 1 is free from any of its undesirable forms.

In an embodiment the lectin protein of SEQ ID NO: 1 or composition comprising lectin protein of SEQ ID NO: 1 is said to be stable when stored in the sealed container of the present invention, at or below room temperature and/or at a relative humidity of 60%, at least for the period of not less than 1 month, if it comprise less than 10%, less than 7%, less than 5%, less than 3% or less than 2% of related substance impurities after such a period of storage. Particularly the related substance impurities are less than 2%.

In an embodiment the lectin protein of SEQ ID NO: 1 or composition comprising lectin protein of SEQ ID NO: 1 is substantially free of impurity proteins of Formula I during its shelf life. In particular embodiment the lectin protein of SEQ ID NO: 1 or composition comprising lectin protein of SEQ ID NO: 1 comprises less than 10%, less than 7%, less than 5%, less than 3% or less than 2% of impurity proteins of Formula I during its shelf life. In a very specific embodiment the lectin protein of SEQ ID NO: 1 or composition comprising lectin protein of SEQ ID NO: 1 comprises less than 2% of impurity proteins of Formula I during its shelf life, wherein Formula I comprises protein of Formula Ia, Formula Ib, Formula Ic, Formula Id or Formula Ie individually or in combination.

It is therefore essential to protect lectin protein of SEQ ID NO: 1 or composition comprising lectin protein of SEQ ID NO: 1 from oxidizing agents such as air, oxidizing chemicals or light. It is also necessary to protect both protein and its composition from higher temperatures, moisture and/or extreme acidic or basic conditions. To lengthen the stability period and increase shelf life of lectin protein of SEQ ID NO: 1 or composition comprising lectin protein of SEQ ID NO: 1, it is essential to maintain temperature, moisture, pH and/or exposure to light waves while preparing, storing and handling, so that the purity of product is consistent and pharmaceutically acceptable throughout the shelf life. Critical attributes such as assay, related substance and HMWP are important in terms of safety and efficacy of the composition and must be maintained throughout the shelf life of the composition.

In a particular embodiment, the present invention provides a stable lectin protein of SEQ ID NO: 1 comprising less than 5% of high molecular weight impurities or related substance impurities individually or in combination when stored at least for a period of about 6 months at a temperature from about 20° C. to about 25° C. and relative humidity of about 60%; wherein the lectin protein is stored in an airtight container that obstructs/resists light waves having wavelength ranging from about 100 nm to about 500 nm; and wherein the headspace in the container comprises vacuum or an inert atmosphere.

In particular embodiment the present invention provides, a composition comprising lectin protein of SEQ ID NO: 1 and a stabilizer, wherein the composition comprises less than 5% of high molecular weight impurities or related substance impurities individually or in combination when stored at least for a period of about 6 months at a temperature from about 20° C. to about 25° C. and relative humidity of about 60%; wherein the composition is stored in an airtight container that obstructs/resists light waves having wavelength ranging from about 100 nm to about 500 nm; and wherein the headspace in the container comprises vacuum or an inert atmosphere.

In another particular embodiment, the present invention provides a lectin protein of SEQ ID NO: 1 comprising less than 5% of high molecular weight impurities or related substance impurities individually or in combination when stored at least for a period of about 1 year at a temperature from about 2° C. to about 8° C.; wherein the lectin protein is stored in an airtight container that obstructs/resists light waves having wavelength ranging from about 100 nm to about 500 nm; and wherein the headspace in the container comprises at least 90% v/v inert gas or vacuum. Inert gases can be selected from helium, nitrogen, argon, or any other suitable gas known in the art.

In another particular embodiment the present invention provides, a composition comprising lectin protein of SEQ ID NO: 1 and a stabilizer, wherein the composition comprises less than 5% of high molecular weight impurities or related substance impurities individually or in combination when stored at least for a period of about 1 year at a temperature from about 2° C. to about 8° C., wherein the composition is stored in an airtight container that obstructs/resists light waves having wavelength ranging from about 100 nm to about 500 nm; and wherein the headspace in the container comprises vacuum or an inert atmosphere.

In more particular embodiment the present invention provides, a lyophilized composition comprising:

a) a lectin protein of SEQ ID NO: 1, and
b) a stabilizer, consisting essentially of an amino acid or its salt, a surfactant, a sugar or carbohydrate or combination thereof, wherein, the composition when placed in an airtight container that obstructs/resists light waves having wavelength ranging from about 250 nm to about 500 nm and the headspace in the container comprises at least 90% v/v inert gas or vacuum, is stable at least for a period of about 6 months at temperature from about 20° C. to about 25° C. and relative humidity of about 60%, and wherein, after such a period, the composition exhibits less than 3% of high molecular weight impurities or related substance impurities individually or in combination.

In another more particular embodiment the present invention provides, a lyophilized composition comprises:

a) a lectin protein of SEQ ID NO: 1, and
b) a stabilizer, consisting essentially of an amino acid or its salt, a surfactant, a sugar or carbohydrate or combination thereof, wherein, the composition, when placed in an airtight container that obstructs/resists light waves having wavelength ranging from about 250 nm to about 500 nm and the headspace in the container comprises at least 90% v/v inert gas or vacuum, is stable at least for a period of about 1 year at temperature from about 2° C. to about 8° C., wherein, after such period, the composition comprises less than 3% of high molecular weight impurities or related substance impurities individually or in combination.

In the most preferable embodiment of the invention, there is provided a stable, lyophilized parenteral composition comprising:

a) about 0.01% w/v to about 2% w/v of a lectin protein of SEQ ID NO: 1,
b) about 0.04% w/v to about 0.8% w/v of polysorbate 80,
c) about 0.08% w/v to about 1.6% w/v of L-arginine hydrochloric acid,
d) about 0.09% w/v to about 19.2% w/v of sucrose, and
e) about 0.09% w/v to about 20% w/v of mannitol, wherein, the composition, when placed in an airtight container that obstructs/resists light waves having wavelength ranging from about 250 nm to about 500 nm and the headspace in the container comprises at least 90% v/v inert gas or vacuum, is stable at least for a period of about 6 months at a temperature from about 20° C. to about 25° C. and relative humidity of about 60%, wherein, after such period, the composition comprises less than 3% of high molecular weight impurities or related substance impurities individually or in combination.

In another most preferable embodiment of the invention, there is provided a stable, lyophilized parenteral composition comprising:

a) about 0.01% w/v to about 2% w/v of lectin protein of SEQ ID NO: 1,
b) about 0.04% w/v to about 0.8% w/v of polysorbate 80,
c) about 0.08% w/v to about 1.6% w/v of L-arginine hydrochloric acid,
d) about 0.09% w/v to about 19.2% w/v of sucrose and
e) about 0.09% w/v to about 20% w/v of mannitol wherein, the composition, when placed in an airtight container that obstructs/resists light waves having wavelength ranging from about 250 nm to about 500 nm and the headspace in the container comprises at least 90% v/v inert gas or vacuum, is stable at least for a period of about 1 year at a temperature from about 2° C. to about 8° C., wherein, after such period, the composition comprises less than 3% of high molecular weight impurities or related substance impurities individually or in combination.

The composition of present invention may further comprise pharmaceutically acceptable excipients. Such excipients may include polymer such as polyethylene glycols (PEGs), dextran, hydroxyl ethyl starch (HETA) or PEG-4000 or combination thereof; and a protein such as human serum albumin or Gelatin or combination thereof.

The compositions of the present invention may further optionally comprise preservatives such as benzyl alcohol, m-cresol, methyl paraben, phenol or combination thereof; tonicity modifier such as sodium chloride, dextrose, potassium chloride, calcium chloride, sucrose, mannitol or combination thereof; a chelating agent such as Ethylene diamine tetra acetic acid; an antioxidant such as ascorbic acid, and/or a cryoprotectant such as mannitol, Ethylene glycol, Glycerol, sucrose, trehalose, and/or dextrose.

It will be appreciated that the examples of the excipients as mentioned herein are for the clarity and understanding of the invention and do not limit the invention in any manner.

The composition of the present invention may be formulated as an aqueous liquid or solid. In some embodiment the composition may be liquid, suspension, powder, sterile powder or lyophilized formulation. Lyophilized formulation may be reconstituted with sterile Water for Injection (WFI) and/or any suitable pharmaceutically acceptable diluent or mixture thereof to get required concentration as known by the skilled person. The composition is suitable for single dose or multiple doses. A person skilled in the art knows that the type of dosing is dependent on various factors, such as the body height and weight, the body surface area, age, gender, or the general health of the patient, and on the preparation to be administered in particular, the duration and type of administration, and on other medications that may be administered in parallel.

The compositions of the present inventions may be administered to an individual in a suitable dosage. The administration can take place locally, enterally, or parenterally, for example, intravenously, intraperitoneally, subcutaneously, intramuscularly, locally, intranasally, intrabronchially or intradermally, or via a catheter at a point in an artery. In particular embodiment the compositions of present inventions may be administered parenterally.

According to an aspect, the present invention provides a method of improving the stability of lectin protein of SEQ ID NO: 1 or of composition comprising lectin protein of SEQ ID NO: 1, wherein the method comprises: storing the lectin protein of SEQ ID NO: 1 or composition comprising lectin protein of SEQ ID NO: 1 in an airtight container that obstructs/resists light waves having wavelength ranging from about 100 nm to about 500 nm and the headspace of the container being vacuum or an inert atmosphere.

According to an embodiment, the stability of lectin protein of SEQ ID NO: 1 is improved for a period of at least 1 month, at least 3 months, at least 6 months, at least 12 months or at least for 24 months. The improvement in the stability of lectin protein has a meaning that the protein remains of pharmaceutically acceptable grade for longer period, its shelf life is considerably increased, and during such longer stability periods the impurity formation is less than the acceptable limits.

According to an embodiment, the stability of composition comprising lectin protein of SEQ ID NO: 1 is improved for a period of at least 1 month, at least 3 months, at least 6 months, at least 12 months or at least for 24 months. The improvement in the stability of the composition has a meaning that the composition remains pharmaceutically acceptable for longer period, its shelf life is considerably increased, and during such longer stability periods the impurity formation is less than the unacceptable limits.

The impurities formed in lectin protein of SEQ ID NO: 1 are preferably HMWP or related substance impurities. In an embodiment the lectin protein of SEQ ID NO: 1 is said to be stable for a period, if at the end of such period it contains not more than 5% of HMWP or related substance impurities individually or in combination.

The impurities formed in the said composition comprising lectin protein of SEQ ID NO: 1 are preferably HMWP or related substance impurities. In an embodiment the composition comprising lectin protein of SEQ ID NO: 1 is said to be stable for a period, if at the end of such period it contains not more than 5% of HMWP or related substance impurities individually or in combination.

In a particular embodiment, the stability of lectin protein of SEQ ID NO: 1 or its composition can be improved for the period of at least about 6 months by placing the airtight container comprising SEQ ID NO: 1 or its composition at room temperature and relative humidity of around 60%. In a more particular embodiment, the stability of lectin protein or its composition can be improved for about 6 months by placing such airtight container at about 20° C. to about 25° C. and relative humidity of around 60%.

In another particular embodiment, the stability of lectin protein of SEQ ID NO: 1 or its composition can be improved for the period of at least about 12 months by placing the airtight container comprising SEQ ID NO: 1 or its composition at below room temperature. In a more particular embodiment, the stability of lectin protein or its composition can be improved for at least about 12 months by placing such airtight container at about 2° C. to about 8° C.

The inventors of the present invention could considerably improve the stability of lectin protein of SEQ ID NO: 1 by storing it under vacuum or in an inert atmosphere in an airtight, opaque container. Exposure of SEQ ID NO: 1 to UV light resulted in formation of impurities up to 11.74 and reduction of assay from 98.61% to 86.87%. Whereas exposure of SEQ ID NO:1 to UV light when stored in opaque container wrapped with aluminium foil formed impurities up to 1.55% and reduced assay from 98.61% to 97.06% only. Similarly, the inventors of the present invention could considerably improve the stability of the composition comprising lectin protein of SEQ ID NO: 1 by storing it under vacuum or an inert atmosphere in an airtight, opaque, amber colour container. Direct exposure of the said composition to UV light resulted in formation of impurities up to 7.56%, whereas indirect exposure in a vial with label resulted in formation of impurities up to 5%. The directly and indirectly exposed composition also showed reduction of assay of the composition from 99% to 89.9% and 93.4%, respectively. Exposure of the composition comprising SEQ ID NO: 1 to UV light when stored in an amber-coloured container did not form impurities or reduce assay.

Long term stability of the composition comprising lectin protein of SEQ ID NO: 1 of the present invention was significantly improved by storing it under vacuum or in an inert atmosphere in an airtight, opaque, amber colour container. Composition comprising lectin protein of SEQ ID NO: 1 stored for 6 months at 25° C./60% RH in a clear vial resulted in formation of total impurities up to 3.60% in comparison to a composition stored in an amber vial that resulted in formation of total impurities up to 1.48%. (2.12% lesser as compared to clear vial).

Assay values of composition comprising lectin protein of SEQ ID NO: 1 when stored in a clear vial reduced from 100.2% to 96.7% in six months. However composition stored in amber vial that resists light of wavelength between 100 nm and 500 nm exhibited minimal change from 101.1% (initial) to 98.6% (six months) in the assay value over period of 6 months.

Similarly, the inventors of the present invention could considerably improve the stability of the composition comprising lectin protein of SEQ ID NO: 1 by storing it under vacuum or in an inert atmosphere in an airtight, opaque, amber colour container. Photostability studies of the said composition in a clear vial without label resulted in formation of impurities up to 1.69% and 1.09% with label. Photostability studies of the said composition in an amber colour vial without label resulted in formation of impurities up to 0.20% and with label resulted in formation of impurities up to 0.20%.

In an embodiment, photostability studies of lectin protein of SEQ ID NO: 1 in a clear vial without label resulted in formation of impurities up to 10.21%, and up to 10.91% with label. The said study carried out on lectin protein of SEQ ID NO: 1, stored in amber vial, showed 0 impurities making it evident that lectin protein of SEQ ID NO: 1 and its composition are light sensitive and packaging of the product in the amber vial helps in controlling critical attributes such as Assay, Related substance, HMWP that are important in terms of safety and efficacy of the composition.

In another embodiment the present invention provides, an airtight container that obstructs/resists light waves having wavelength ranging from about 100 nm to about 500 nm, comprising lectin protein of SEQ ID NO: 1 and a headspace, wherein the headspace comprises vacuum or an inert atmosphere.

In another embodiment the present invention provides, an airtight container that obstructs/resists light waves having wavelength ranging from about 100 nm to about 500 nm, wherein the container comprises composition comprising lectin protein of SEQ ID NO: 1 and a headspace, wherein the headspace comprises vacuum or an inert atmosphere.

In another embodiment, there is provided a method of packaging a lectin protein of SEQ ID NO 1 or a pharmaceutical composition comprising the lectin protein of SEQ ID NO: 1, wherein the method comprises:

a) placing the lectin protein or composition thereof in a container that obstructs/resists light waves having wavelength ranging from about 100 nm to about 500 nm, and
b) sealing the container such that the lectin protein of SEQ ID NO 1 or the composition remains in contact with an inert atmosphere or vacuum.

In an embodiment, the container comprising lectin protein or its composition is an airtight container. The airtight container is container with an airtight seal, which does not allow air or gas to pass in and out of the container. Thus, the conditions in the container are maintained from the time of sealing, throughout storage, handling and until it is opened for use. In particular embodiment the method of packaging comprises placing the lectin protein or its composition in an airtight container that obstructs/resists light waves having wavelength ranging from about 100 nm to about 500 nm.

In another embodiment, the lectin protein or its composition in an airtight container is in contact with vacuum. The vacuum is applied to such container by the methods known to the skilled person; or the protein or its composition in the container is lyophilized and freed from moisture under vacuum or an inert atmosphere, wherein the lectin protein or its composition as solution is freezed to below −20° C. for about 20 h to 40 h followed by sublimation under vacuum of about 0.05 mbar to 0.2 mbar for up to 60 h and finally dried under vacuum of about 0.05 mbar to 0.2 mbar for up to 20 h.

In an embodiment, the method of packaging might further comprise a secondary container, wherein the airtight container comprising SEQ ID NO: 1 is placed in the secondary container. The secondary container may be of paper, cardboard, wood, plastic or light obstructing/restricting glass. More preferably, the secondary container may be a carton a plastic box or an aluminium pouch.

According to an aspect, there is provided a method of preparation of a stable lyophilized composition comprising:

a) a lectin protein of SEQ ID NO: 1, and
b) a stabilizer, consisting essentially of an amino acid or its salt, a surfactant, a sugar or carbohydrate or combination thereof, wherein, the method comprises formulating the composition under the light having wavelength of more than about 500 nm.

In an embodiment of the present invention, there is provided a process to prepare stable lyophilized composition, wherein the process comprises: combining buffer solution of lectin protein of SEQ ID NO: 1 with the buffer solution of one or more of the stabilizers under the light having wavelength of more than about 500 nm or more than about 589 nm or particularly under Sodium vapour lamp. The process is carried out at room temperature. The composition in the solution form is optionally lyophilized. The lyophilization can be carried out either in a tray or in the airtight container of the present invention.

EXAMPLES

Examples are for the purpose of demonstration and to illustrate the mode of invention only. They do not restrict the scope of the invention in any manner.

Analysis of the samples was carried out using HPLC method. HPLC system with UV detector was used with column C4, 3.5ρ, 150×4.6 mm (Make: Kromasil or equivalent). Mobile phases used were: mixture of 1 mL of trifluroacetic acid and 1000 mL of purified water, or 1 mL of trifluroacetic acid to 1000 mL of acetonitrile. The skilled person is well aware of the other methods, instruments and techniques to analyse protein samples. The HPLC method could be varied based on the necessity of the experiment and understanding of the skilled person. The machinery, equipment and instrumentation and method of analysis used herein does not limit the scope of the invention in any manner.

Lectin Protein of SEQ ID NO 1 was prepared by the process disclosed in WO/2020/074977.

Example 1: Formulation of Recombinant Protein

| Ingredients | Composition in mg/mL [after reconstitution of lyophilised composition in 1 ml of sterile water for injection] |
|---|---|
| SEQ ID NO. 1 | 2.50 |
| Tris | 1.31 |
| NaCl | 1.90 |
| Polysorbate 80 | 1 |
| L-Arginine HCl | 2 |

-continued

| Ingredients | Composition in mg/mL [after reconstitution of lyophilised composition in 1 ml of sterile water for injection] |
|---|---|
| Sucrose | 24 |
| Mannitol | 72 |
| Hydrochloric acid | q.s. to pH |

The above formulation was prepared by the following process, while every step was carried out under Sodium vapour lamp:

a) stock solution of Polysorbate 80 (10% w/v) was prepared in WFI. Required quantity of Polysorbate 80 was taken from this stock solution and added in the WFI.
b) stock solution of protein of SEQ ID NO. 1 was prepared in TBS (Tris buffer saline) and was taken into a glass beaker;
c) required quantity of solution of protein of SEQ ID NO. 1 of step b) was added to the required quantity of solution of step a) at a temperature of 22° C.-25° C. and mixed well to obtain clear colourless solution appeared;
d) required quantity of L-Arginine HCl was added to the solution of step c) and was mixed well for homogenous dissolution;
e) required quantity of Sucrose was added to the solution of step d) and mixed well for homogenous dissolution;
f) required quantity of mannitol was added to the solution of step e) and mixed to get clear colourless solution;
g) the volume of the batch was made up to 80% of batch size using water for injection (WFI);
h) pH of the solution in step g) was adjusted between 7.4-8.5 using 0.05N HCl (The pH is be adjusted to 7.4 to 8.5 using 0.05 N NaOH if the solution in step g) is acidic);
i) WFI was added to solution in step h) to make up the batch size and filtered through 0.2 micron poly ether sulphone (PES) filter;
j) batch was filled in the vials (airtight container) and subjected for lyophilisation. The lyophilisation inherently involved application of vacuum in primary and secondary drying steps. After completion of the secondary drying, sealing of vials was done under vacuum, and hence, the headspace in vials comprises vacuum.
k) lyophilized vials were stored at room temperature or 2° C.-8° C. temperature.

Example 2: Photostability Study of Formulation of Example 1

Photostability study was performed as per ICH Q1B, wherein the product was packed in two types of container (clear and amber colored glass vials) with four different specification as below:

1. Vial wrapped in Aluminum Foil as a control
2. Vial without Label
3. Vial with Label
4. Vial with Label in secondary carton.

All above packs were exposed to light providing an overall illumination of not less than 1.2 million lux hours and an integrated near ultraviolet energy of not less than 200 watt hours/square meter for 120 hrs. The samples after 120 hrs were analysed using HPLC method. The results obtained are shown in Table 1 and Table 2.

TABLE 1

Photostability Data of lyophilized composition (drug product) in clearvial

| Details | Aluminium Wrap | Vial without Label | Vial with Label | Labelled vial in secondary carton |
|---|---|---|---|---|
| pH | 7.693 | 7.688 | 7.692 | 7.701 |
| Assay (90-110%) | 99.0 | 89.9 | 93.4 | 98.2 |
| HMWP impurity (NMT 2%) | 0.38 | 0.18 | 0.05 | 0.27 |
| RS % Individual Unknown max. Impurity (NMT 2%) | 0.05 | 7.56 | 4.96 | 0.05 |
| % Total Impurity (NMT 5%) | 0.05 | 7.56 | 5.01 | 0.05 |

TABLE 2

Photostability Data of lyophilizedcomposition (drug product) in Amber coloured vial

| Details | Aluminium Wrap | Vial without Label | Vial with Label | Labelled vial in secondary carton |
|---|---|---|---|---|
| pH | 7.787 | 7.674 | 7.560 | 7.727 |
| Assay (90-110%) | 98.8 | 98.5 | 95.8 | 97.8 |
| HMWP impurity (NMT 2%) | 0.37 | 0.37 | 0.41 | 0.44 |
| RS % Individual Unknown max. impurity (NMT 2%) | 0.11 | 0.10 | 0.09 | 0.10 |
| % Total Impurity (NMT 5%) | 0.19 | 0.17 | 0.17 | 0.18 |

Conclusion: Direct exposure of the composition to UV light resulted in formation of impurities up to 7.56%, whereas indirect exposure in a vial with label resulted in formation of impurities up to 5%. The directly and indirectly exposed composition also showed reduction of assay of the composition from 99% to 89.9% and to 93.4%, respectively. Exposure of composition comprising SEQ ID NO:1 to UV light when stored in an amber-coloured container (which resists light of wavelength between 100 nm and 500 nm) did not form impurities or showed reduction in assay.

Example 3: Stability Studies of Formulation of Example 1

The lyophilised formulation of Example 1 was stored in Clear Vial (5 ml 20 mm clear lyophilizedvial of USP Type I from Schott) and Amber Vial (5 ml 20 mm amber lyophilized vial of USP Type I from Schott) at 25° C.±2° C. and Relative Humidity (RH) of 60±5% and at 2° C. to 8° C. The sample from both the bottles were analysed using HPLC method after 6 months to assess its stability.

TABLE 3

| Long term and accelerated Stability data at 25° C./60% RH | | | | | | | | |
|---|---|---|---|---|---|---|---|---|
| | Clear Vial Drug Product | | | | Amber Vial Drug Product | | | |
| | | 25° C./60% RH | | | | 25° C./60% RH | | |
| Test | Initial | 1 M | 3 M | 6 M | Initial | 1 M | 3 M | 6 M |
| Appearance | * | * | * | * | * | * | * | * |
| pH | 7.76 | 7.97 | 7.92 | 7.84 | 8.11 | 7.87 | 7.88 | 7.93 |
| Assay | 100.2 | 97.5 | 98.1 | 96.7 | 101.1 | 99.8 | 100.5 | 98.6 |
| HMWP | 0.27 | 0.78 | 1.31 | 1.33 | 0 | 0.08 | 0.21 | 0.52 |
| RS Single Max | 0.49 | 0.58 | 0.89 | 1 | 0.44 | 0.59 | 0.49 | 0.58 |
| Total Impurity | 1.45 | 1.97 | 2.64 | 3.60 | 0.87 | 0.92 | 1.30 | 1.48 |

*white lyophilized cake

Figure 2:
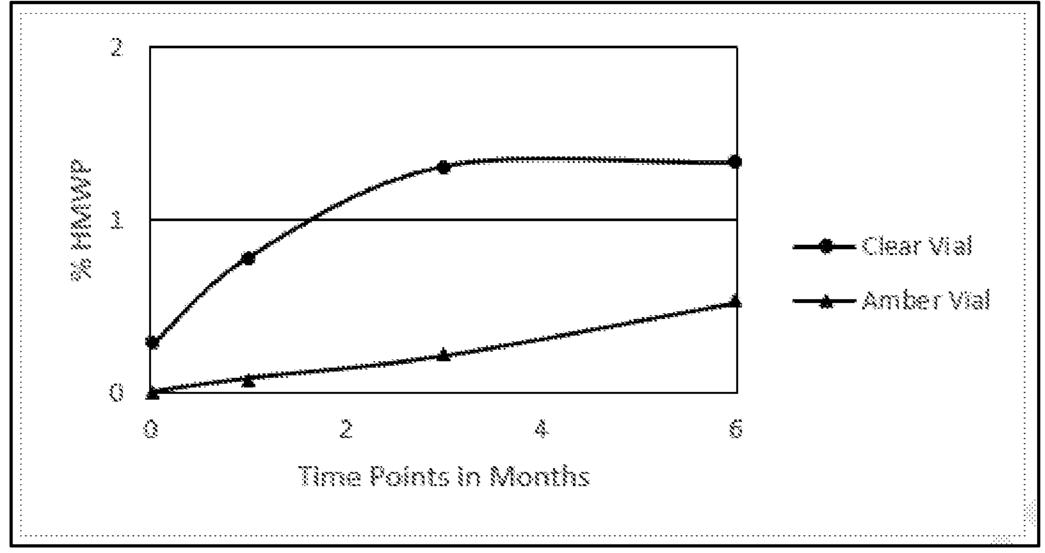
FIG. 2: HMWP of composition stored in Clear versus Amber vial at 25° C./60% RH
Figure 3:
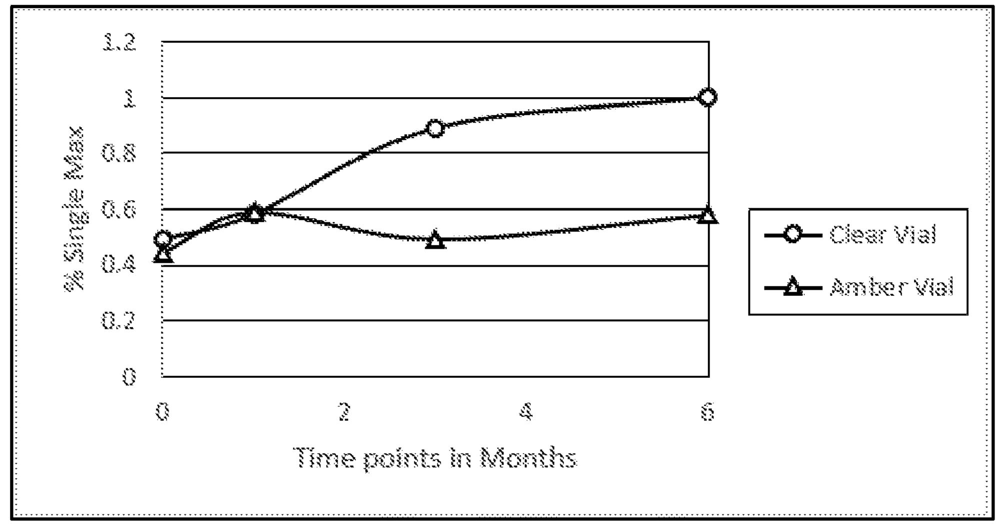
FIG. 3: Single max impurity of composition stored in Clear versus Amber vial at 25° C./60% RH
Figure 4:
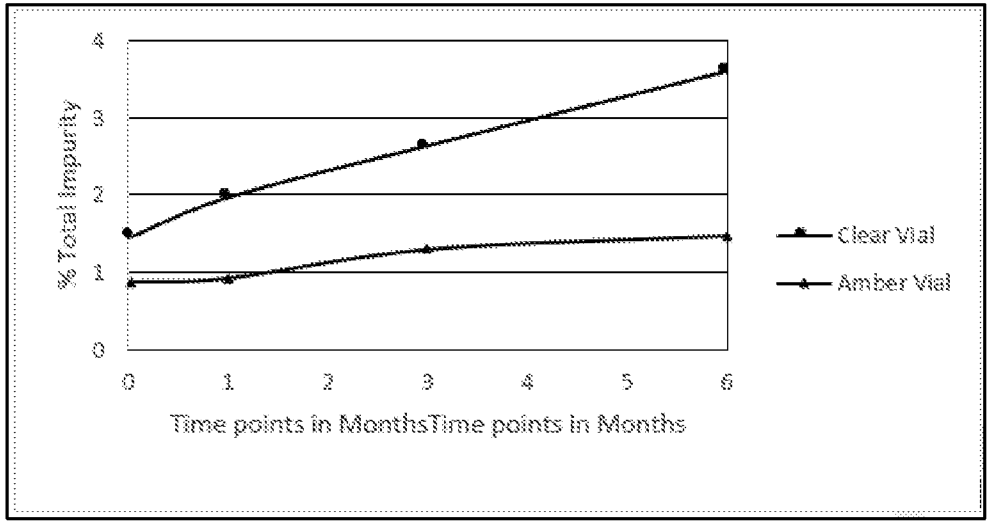
FIG. 4: Total impurity of composition stored in Clear versus Amber vial at 25° C./60% RH

Conclusion:

[Refer: FIGS. 1, 2, 3 & 4]

Long term and accelerated Stability studies of composition of lectin protein of SEQ ID NO: 1 stored in clear & amber vial for 6 months at 25° C./60% RH resulted in formation of total impurities up to 3.60% and 1.48% respectively. Assay value found consistent with throughout 6 months in amber vial. On the other hand, assay values in clear vials reduced to 96.7% from 100.2% in 6 months. HMWP in the amber vial were much lower as compared to clear vial.

TABLE 4

| Long term and accelerated Stability data at 2-8° C. | | | | | | | | | | |
|---|---|---|---|---|---|---|---|---|---|---|
| | | Clear Vial Drug Product | | | | Amber Vial Drug Product | | | | |
| | | 2-8° C. | | | | | 2-8° C. | | | |
| Test | Initial | 1 M | 3 M | 6 M | 12 M | Initial | 1 M | 3 M | 6 M | 12 M |
| Appearance | * | * | * | * | * | * | * | * | * | * |
| pH | 7.76 | ND | 7.93 | 7.77 | 7.82 | 8.11 | 7.91 | 7.76 | 7.97 | 7.74 |
| Assay | 100.2 | 99.2 | 100.4 | 99.6 | 100.7 | 101.1 | 103 | 100.3 | 100 | 100.1 |
| HMWP | 0.27 | 0.33 | 0.54 | 0.55 | 0.67 | 0 | 0.17 | 0.10 | 0.08 | 0.06 |
| RS Single Max | 0.49 | 0.47 | 0.53 | 0.46 | 0.73 | 0.44 | 0.59 | 0.50 | 0.53 | 0.44 |
| Total | 1.45 | 1.45 | 1.50 | 1.87 | 2.30 | 0.87 | 0.95 | 0.95 | 1.03 | 0.95 |

*white lyophilized cake

Figure 5:
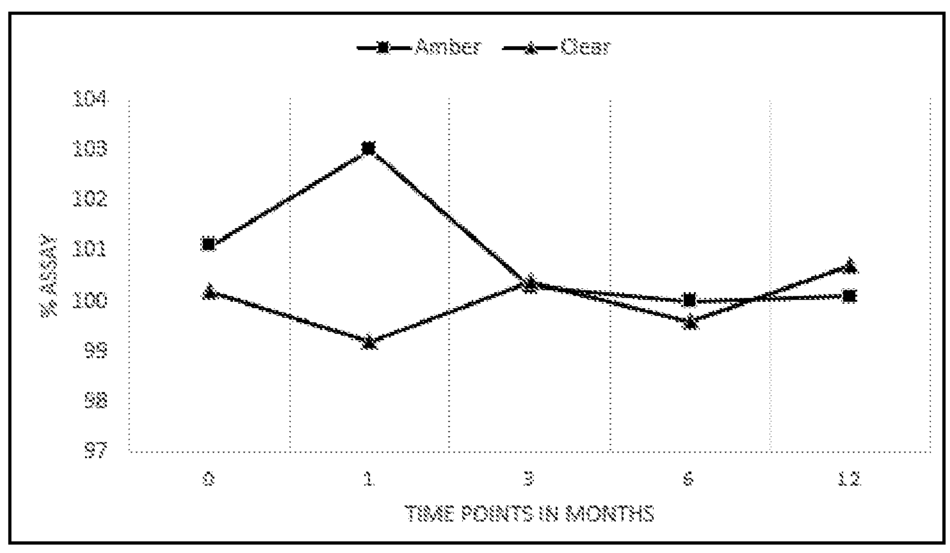
FIG. 5: Assay results of composition stored in Clear versus Amber vial at 2-8° C.
Figure 6:
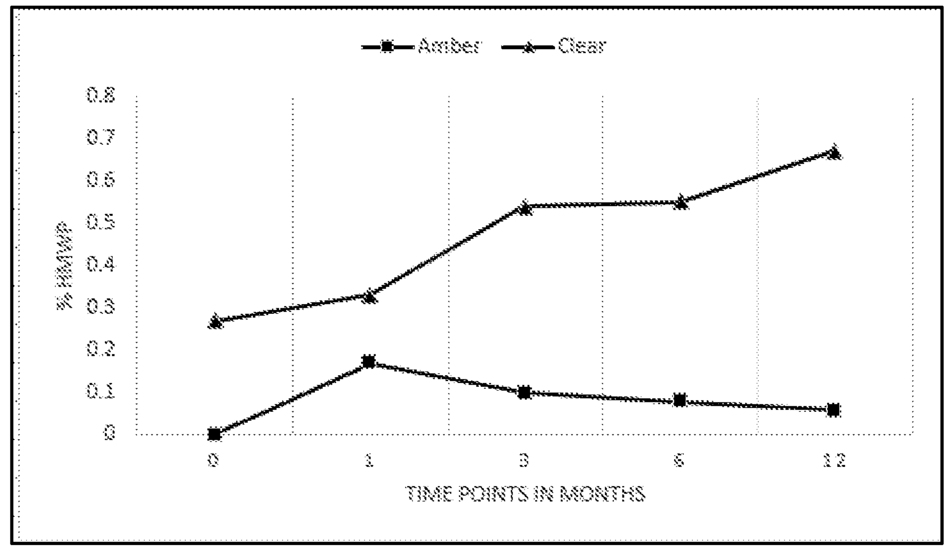
FIG. 6: HMWP of composition stored in Clear versus Amber vial at 2-8° C.
Figure 7:
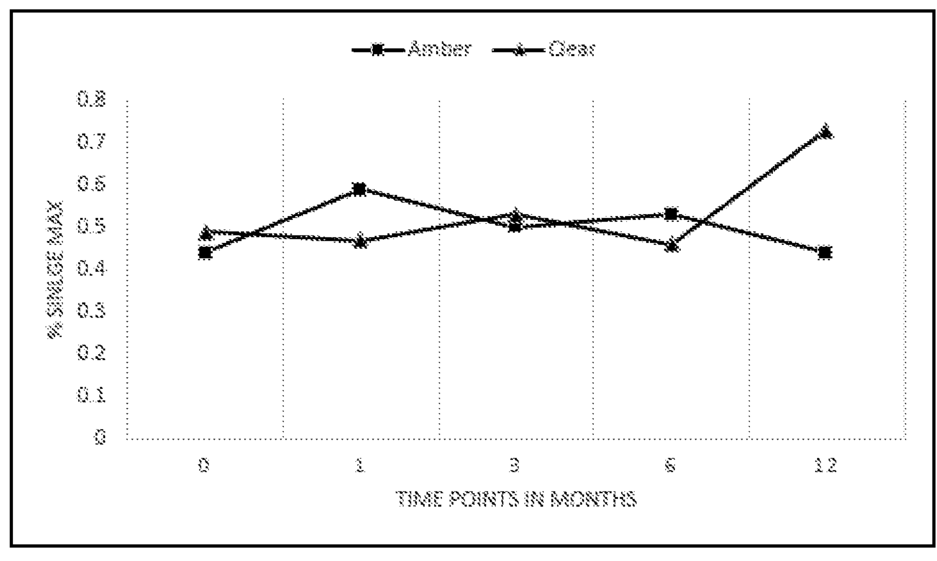
FIG. 7: Single max impurity of composition stored in Clear versus Amber vial at 2-8° C.
Figure 8:
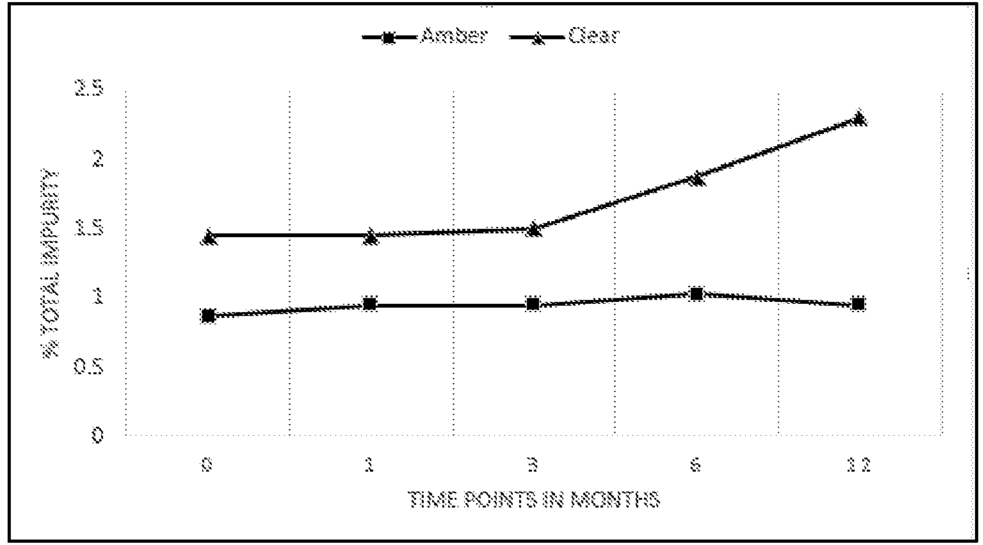
FIG. 8: Total impurity of composition stored in Clear versus Amber vial at 2-8° C.

Conclusion:

[Refer FIGS. 5, 6, 7 & 8]

Conclusion: In Long term and accelerated Stability studies data both Clear vial and amber vial with label, in secondary carton kept on stability. Lectin protein of SEQ ID NO 1 found stable in both containers. Critical attributes like Assay, Related substance and HMWP are more controlled in amber vial than clear vial making it evident from data that Lectin protein of SEQ ID NO 1 and its Lyophilized composition are light sensitive. Storage of the product in amber vial helps in preventing light exposure to Lectin protein of SEQ ID NO land improves stability of drug product. This helps in the controlling critical attributes like Assay, Related Substances, HMWP which are important in terms of Safety and efficacy of composition.

Example 5: Forced Degradation Studies of Lectin Protein of SEQ ID NO 1

Example 5a: Photo Degradation

Lectin Protein of SEQ ID NO 1 diluted with diluent comprising Tris 25 mM pH 8.0 Buffer was exposed to white light 1.2 million lux hours and near ultraviolet energy 200-watt hours/square meter for 120 hrs at 25±2° C. In another experiment before exposing the sample was wrapped with aluminium foil. As a control the sample was analysed without exposure to light. The analysis of samples after 120 hrs of exposure gave following results:

TABLE 5

| Control | | | | | |
|---|---|---|---|---|---|
| RT | RRT | % Area | Peak Purity | Blank | % Degradation against control |
| 19.747 | 1.000 | 98.61 | Peak pure | No | NA |
| 20.040 | 1.015 | 0.92 | Peak Impure | Peak | |
| 20.260 | 1.026 | 0.47 | Peak Impure | found | |

TABLE 6

| Photo degradation analysis of Sample stored in amber colored vial wrapped with Aluminium foil | | | | | |
|---|---|---|---|---|---|
| RT | RRT | % Area | Peak Purity | Blank | % Degradation against control |
| 19.340 | 0.980 | 0.04 | Peak Impure | No | 1.55 |
| 19.733 | 1.000 | 97.06 | Peak pure | Peak | |
| 19.933 | 1.010 | 1.13 | Peak Impure | found | |
| 20.027 | 1.015 | 0.92 | Peak Impure | | |
| 20.253 | 1.026 | 0.84 | Peak Impure | | |

TABLE 7

| Photo degradation analysis of Sample without Aluminium foil Wrapped | | | | | |
|---|---|---|---|---|---|
| RT | RRT | % Area | Peak Purity | Blank | % Degradation against control |
| 19.573 | 0.992 | 12.65 | Peak Impure | No | 11.74 |
| 19.727 | 1.000 | 86.87 | Peak pure | peak | |
| 20.007 | 1.014 | 0.32 | Peak Impure | found | |
| 20.213 | 1.025 | 0.15 | Peak Impure | | |

Conclusion: Exposure of SEQ ID NO: 1 to UV light resulted in formation of impurities up to 11.74 and reduction of assay from 98.61% to 86.87%. Whereas exposure of SEQ ID NO:1 to UV light when stored in opaque container wrapped with aluminium foil formed impurities up to 1.55% and reduced assay from 98.61% to 97.06% only.

Lectin protein of SEQ ID NO: 1 with about 12% of Met-lectin variant was exposed to white light of 1.2 million lux hours and near ultraviolet energy of 200-watt hours/square meter for 120 hrs, the protein degraded by 11.74% hinting at photo catalysed oxidation of initiator methionine.

Example 5b. Oxidation Degradation

To 400 μL of sample solution containing 10 mg/mL of SEQ ID NO: 1 in diluent comprising tris 25 mM pH 8.0 buffer was added 800 μL of 3% hydrogen peroxide solution. The Sample was incubated at room temperature for 10 mins and was neutralize using solution of 30.1 mg of methionine in 800 μL of diluent. The control solution used for analysis contained 400 ML of sample solution containing 10 mg/mL of SEQ ID NO: 1 and 1600 μL of diluent. The results against control are as given below:

TABLE 8

| Control | | | | | |
|---|---|---|---|---|---|
| RT | RRT | % Area | Peak Purity | Blank | % Degradation against control |
| 18.873 | 0.981 | 0.07 | Peak Impure | No peak | NA |
| 19.240 | 1.000 | 98.50 | Peak Pure | | |
| 19.493 | 1.013 | 0.88 | Peak Impure | | |
| 19.613 | 1.019 | 0.34 | Peak Impure | | |
| 19.820 | 1.030 | 0.21 | Peak Impure | | |

TABLE 9

| Oxidation degradation analysis of Sample | | | | | |
|---|---|---|---|---|---|
| RT | RRT | % Area | Peak Purity | Blank | % Degradation against control |
| 17.473 | 0.908 | 0.25 | Peak Impure | No | 14.13 |
| 17.553 | 0.912 | 0.26 | Peak Impure | peak | |
| 18.607 | 0.967 | 0.47 | Peak Impure | | |
| 18.747 | 0.974 | 0.68 | Peak Impure | | |
| 18.953 | 0.985 | 1.48 | Peak Impure | | |
| 19.153 | 0.995 | 6.05 | Peak Impure | | |
| 19.240 | 1.000 | 84.37 | Peak Pure | | |
| 19.427 | 1.010 | 4.44 | Peak Impure | | |
| 19.753 | 1.027 | 1.82 | Peak Impure | | |
| 20.220 | 1.051 | 0.2 | Peak Impure | | |

Conclusion:

Lectin protein of SEQ ID NO: 1 was subjected to oxidation using 3% hydrogen peroxide at room temperature for about 10 min, the protein degraded by more than 14% as compared to the control, hinting towards partial oxidation of methionine at position 44 and 89 in SEQ ID NO: 1.

Example 6: Photo Stability Studies of Drug Substance and Drug Product

Photo stability studies were done on Drug substance and Drug product packed in clear and light resistant amber colour glass vials.

TABLE 10

| Photo stability of Drug substance manufactured using clear & light resistant amber vials. | | | | | | | | | |
|---|---|---|---|---|---|---|---|---|---|
| | | Clear Vial Drug Substance | | | | Amber Vial Drug Substance | | | |
| Test | | Aluminium Wrap | without Label | with Label | Label + Carton | Aluminium Wrap | without Label | with Label | Label + Carton |
| Description | | * | * | * | * | * | * | * | * |
| RS | % Total Impurity | 0 | 10.21 | 10.91 | 0 | 0 | 0 | 0 | 0 |

* clear colorless solution

Conclusion: Photostability studies of the lectin protein of SEQ ID NO: 1 stored in clear vial without label resulted in formation of impurities up to 10.21% and 10.91% with label. Photostability studies of the lectin protein of SEQ ID NO: 1 stored in light resistant amber vial resulted in formation on 0% impurities with and without label.

TABLE 11

Photo stability of Drug product manufactured using clear & amber vials.

| Test | Clear Vial Drug Product | | | | | Amber Vial Drug Product | | | | |
|---|---|---|---|---|---|---|---|---|---|---|
| | Initial | Aluminium Wrap | without Label | with Label | Label + Carton | Initial | Aluminium Wrap | without Label | with Label | Label + Carton |
| Description | * | * | * | * | * | * | * | * | * | * |
| RS % Total Impurity | 0.16 | 0.17 | 1.69 | 1.09 | 0.21 | 0.17 | 0.19 | 0.20 | 0.20 | 0.21 |

* white lyophilized cake

Conclusion: Photo stability studies of the composition in a clear vial without label resulted in formation of impurities up to 1.69% and with label resulted in formation of impurities up to 1.09%. Photostability studies of the said composition in a light resistant amber colour vial without label resulted in a formation of impurities up to 0.20% and 0.20% with label making it evident that lectin protein of SEQ ID NO: 1 light sensitive and storage of the product in the light resistant amber vial helps in controlling critical attributes such as Assay, Related substance, HMWP that are important in terms of safety and efficacy of the composition.

We claim:

1. A method for stabilizing a composition comprising a recombinant lectin protein of SEQ ID NO: 1 and stabilizing agent(s) during storage or exposure to light, comprising:

a. introducing the composition into a container to obtain a stabilized composition, wherein i. the container resists light waves of wavelength between 100 nm and 500 nm;

ii. a headspace of the container comprises inert atmosphere or vacuum; and iii. the stabilizing agent(s) comprises an amino acid or its salt; a surfactant; a sugar or carbohydrate; or a combination thereof;

wherein the stabilized composition exhibits less than 5% of high molecular weight impurities or related substance impurities individually or in combination, optionally, when the composition is stored for a period of 6 months at a temperature ranging from 20° C.-25° C. and relative humidity of 60% or when the composition is stored for a period of 1 year at 2° C.-8° C.

2. The method of claim 1, wherein the container is selected from a vial, syringe, cartridge, ampule.

3. The method of claim 1, wherein the composition exhibits less than 5% of high molecular weight impurities or relative substance impurities individually or in combination when the composition is stored for a period of 6 months at a temperature ranging from 20° C.-25° C. and relative humidity of 60% or when the composition is stored for a period of 1 year at 2° C.-8° C.

4. The method of any of claim 1, wherein the composition comprises a. 0.01% w/v to 2% w/v of lectin protein of SEQ ID NO: 1; b. 0.04% w/v to 0.8% w/v of polysorbate 80; c. 0.08% w/v to 1.6% w/v of L-arginine hydrochloric acid, d. 0.09% w/v to 19.2% w/v of sucrose, and e. 0.09% w/v to 20% w/v of mannitol.

* * * * *